(12) United States Patent
Daley et al.

(10) Patent No.: US 11,948,674 B2
(45) Date of Patent: *Apr. 2, 2024

(54) SURGICAL PROCEDURE PLANNING SYSTEM WITH MULTIPLE FEEDBACK LOOPS

(71) Applicant: MAKO Surgical Corporation, Fort Lauderdale, FL (US)

(72) Inventors: Robert J. Daley, Burr Ridge, IL (US); Sean M. Daley, Burr Ridge, IL (US)

(73) Assignee: MAKO Surgical Corporation, Weston, FL (US)

( * ) Notice: Subject to any disclaimer, the term of this patent is extended or adjusted under 35 U.S.C. 154(b) by 168 days.

This patent is subject to a terminal disclaimer.

(21) Appl. No.: 17/487,706

(22) Filed: Sep. 28, 2021

(65) Prior Publication Data

US 2022/0084652 A1 Mar. 17, 2022

Related U.S. Application Data

(63) Continuation of application No. 15/898,288, filed on Feb. 16, 2018, now Pat. No. 11,158,415.

(Continued)

(51) Int. Cl.
*G16H 20/40* (2018.01)
*A61B 5/00* (2006.01)
*A61B 8/08* (2006.01)
*A61B 17/17* (2006.01)
*A61B 34/10* (2016.01)

(Continued)

(52) U.S. Cl.
CPC ........... *G16H 20/40* (2018.01); *A61B 5/0082* (2013.01); *A61B 8/0875* (2013.01); *A61B 17/17* (2013.01); *A61B 34/10* (2016.02); *A61B 34/30* (2016.02); *A61B 34/32* (2016.02); *A61B 90/37* (2016.02); *A61F 2/24* (2013.01); *G16H 40/20* (2018.01); *G16H 50/50* (2018.01); *A61B 5/1121* (2013.01); *A61B 5/4585* (2013.01); *A61B 2034/105* (2016.02); *A61B 2034/108* (2016.02);

(Continued)

(58) Field of Classification Search
CPC ........ G16H 20/40; G16H 40/20; G16H 50/50; A61B 34/10; A61B 34/30; A61B 34/32; A61B 90/37; A61B 5/0082; A61B 8/0875; A61B 17/17; A61B 2034/105; A61B 2034/108; A61B 2034/256; A61B 2090/365; A61B 5/1121; A61B 5/4585; A61B 2505/05; A61F 2/24
USPC ............................................................ 705/2
See application file for complete search history.

(56) References Cited

U.S. PATENT DOCUMENTS 3,774,244 A 11/1973 Walker
6,879,959 B1 4/2005 Chapman et al.
(Continued)

FOREIGN PATENT DOCUMENTS

WO WO 2008/039243 A1 4/2008

OTHER PUBLICATIONS

Sep. 12, 2016—(PCT) International Search Report and Written Opinion, App. No. PCT/US2016/032331.

*Primary Examiner* — Peter H Choi
*Assistant Examiner* — Rachael Sojin Stone
(74) *Attorney, Agent, or Firm* — Bookoff McAndrews, PLLC (57) ABSTRACT

A surgical procedure planning system and method that uses multiple feedback loops to optimize creation or design of future surgical preoperative plans.

20 Claims, 3 Drawing Sheets

Related U.S. Application Data (60) Provisional application No. 62/459,891, filed on Feb. 16, 2017.

(51) Int. Cl.

| | | |
|---|---|---|
| *A61B 34/30* | (2016.01) | |
| *A61B 34/32* | (2016.01) | |
| *A61B 90/00* | (2016.01) | |
| *A61F 2/24* | (2006.01) | |
| *G16H 40/20* | (2018.01) | |
| *G16H 50/50* | (2018.01) | |
| *A61B 5/11* | (2006.01) | |
| *A61B 34/00* | (2016.01) | |

(52) U.S. Cl.
CPC ... *A61B 2034/256* (2016.02); *A61B 2090/365* (2016.02); *A61B 2505/05* (2013.01)

(56) References Cited

U.S. PATENT DOCUMENTS

| | | |
|---|---|---|
| 7,388,972 B2 | 6/2008 | Kitson |
| 2002/0114845 A1 | 8/2002 | DeVore et al. |
| 2004/0030245 A1 | 2/2004 | Noble et al. |
| 2004/0068187 A1 | 4/2004 | Krause et al. |
| 2008/0077158 A1 | 3/2008 | Haider et al. |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0250276 A1 | 9/2010 | Pierce et al. |
| 2010/0250284 A1 | 9/2010 | Pierce et al. |
| 2010/0250571 A1 | 9/2010 | Pierce et al. |
| 2011/0077504 A1 | 3/2011 | Fischer et al. |
| 2013/0297538 A1 | 11/2013 | Gosink et al. |
| 2013/0345718 A1* | 12/2013 | Crawford ............... A61B 5/061 606/130 |
| 2014/0081659 A1* | 3/2014 | Nawana ............... A61B 5/4833 705/3 |
| 2015/0051650 A1 | 2/2015 | Verstreken et al. |
| 2015/0057675 A1 | 2/2015 | Akeel et al. |
| 2016/0034664 A1 | 2/2016 | Santos et al. |
| 2016/0283676 A1 | 9/2016 | Lyon et al. |
| 2016/0331474 A1 | 11/2016 | Lacal et al. |
| 2017/0056116 A1 | 3/2017 | Kostrzewski |
| 2017/0185729 A1 | 6/2017 | Boray et al. |
| 2018/0032841 A1 | 2/2018 | Kluckner et al. |
| 2018/0303552 A1 | 10/2018 | Ryan et al. |
| 2020/0261119 A1* | 8/2020 | Pavlovskaia ............ A61B 6/505 |
| 2021/0169505 A1 | 6/2021 | Tikka |
| 2023/0301719 A1* | 9/2023 | Murphy ............... A61B 34/20 606/1 |

* cited by examiner

SURGICAL PROCEDURE PLANNING SYSTEM WITH MULTIPLE FEEDBACK LOOPS

CROSS-REFERENCE TO RELATED APPLICATION(S)

This patent application is a continuation of and claims the benefit of priority to U.S. Nonprovisional patent application Ser. No. 15/898,288, filed Feb. 16, 2018, which claims the benefit of priority to U.S. Provisional 62/459,891, filed Feb. 16, 2017, the entireties of which are incorporated herein by reference.

BACKGROUND

In surgical disciplines, surgical procedures are affected by the uncertainty associated with complex variability between patient's anatomy, injury disease state, and functionality. In other words, even though a defined surgical procedure on a patient may be a generally defined procedure with a defined order of steps for a defined anatomical patient part, uncertainty almost always exists because patient's anatomy at least slightly differs, each patient's injury or disease state at least slightly differs, and the functionality of each patient's anatomy at least slightly differs. This uncertainty often arises in the ability to correctly create or design a preoperative plan to produce the optimal result for a specific patient. This uncertainty over the complex variability and the hierarchy of prioritizing preoperative plan creation or design decisions is one of the greatest sources of potential error and risk associated with creating a preoperative plan.

In creating a preoperative plan, many issues typically need to be considered, addressed, or determined. In every surgical specialty, there are general rules that typically guide how the preoperative plan addresses these issues. For example, the preoperative plan for a knee replacement typically includes an identification of the anatomic axis of the femur (i.e., the thigh bone) and the mechanical (weight bearing) axis. The preoperative plan also typically includes an assessment of the rotational alignment for the femur that affects stability of the knee and the motion of the kneecap (i.e., the patella). The preoperative plan also typically includes an evaluation of the size, orientation, and proportions of the bones. The preoperative plan also typically includes a proposed depth of bone resection on the femur that relates to balancing ligament tension, soft tissue balance, stability to the knee, and a component that fits the femur without undue irritation to the surrounding tissue. The preoperative plan also typically includes a determination of tibial (i.e., shin bone) axis and the angle of the bone preparation of the tibia that similarly effects balancing ligament tension, soft tissue balance, stability to the knee and a component that fits the tibia without undue irritation to the surrounding tissue. The preoperative plan also typically includes chosen sizes for each of the components and assignments for the three-dimensional placement of the components. The components are placed with these and potentially many more considerations on every patient to facilitate a safe procedure and postoperative course and as well as maximal function of the knee.

One of the known ways to address preoperative plan creation and design uncertainty has been through the aggregate prediction based on one or more known preoperative plan sets. Each of these known preoperative plan sets include a plurality of different individual preoperative plans for the same surgical procedure (such as a left knee replacement or a right hip replacement), where each individual preoperative plan of the set provides a unique preoperative plan based on automated or software based analysis of complex anatomy and function of the particular surgical site for the particular patient. The aggregate preoperative plan obtained from or based on such a preoperative plan set can in certain instances provide a better overall predictive performance and can exhibit less bias than the preoperative plan set's individual constituents because the aggregate is derived from a weighted combination of all the preoperative plan set members.

While such aggregated preoperative plans provide more accurate estimates for prediction and forecasting for future individual patient preoperative plans, these aggregates do not help automated and/or manual preoperative plan creators or designers refine and improve the individual preoperative plans (such as for robotically assisted surgical procedures) that initially make up or form the preoperative plan set.

Accordingly, there is a need to solve these problems and to provide better preoperative plans that can be aggregated and used to create or design future preoperative plans.

SUMMARY

Various embodiments of the present disclosure solve the above problems by providing a surgical procedure planning system and method with multiple feedback loops for optimizing future surgical preoperative plans. Various embodiments of the present disclosure provide a system and method that utilizes the benefits of certain aggregation techniques to provide feedback to preoperative plan creators or designers, so that they can better understand various factors and hierarchy to improve the individual preoperative plans that form or are used as preoperative plans in or for development of future preoperative plan sets, and thus for the development of future enhanced individual preoperative plans for individual patients.

While aggregating preoperative plans for sets of similar anatomical conditions can assist in producing models for future preoperative plans, such steps do not by themselves fully optimize outcomes. Thus, in various embodiments of the present disclosure, the system and method facilitates modeling done on aggregated selected preoperative plans based on existing rules which prioritize decisions made in the planning process. And, in various other embodiments of the present disclosure, the system and method facilitates modeling done on aggregate preoperative plans based on one or more surgeon selected prioritized desired outcomes that cause the system and method to determine which of the system stored preoperative plans to select for aggregation based on the patient outcomes that resulted from the use of those stored preoperative plans. For example, in certain such embodiments, the system and method determines which of the system stored preoperative plans to select for aggregation by selecting one or more specific stored preoperative plans that needed the fewest revisions to their respective initial preoperative plans (on which they were based) and that resulted in the best patient reported outcomes. In certain such embodiments, the system and method uses suitable machine learning to optimize and determine a new hierarchy of decisions for preoperative planning for subsequent patients who share specific common features tracked by the system and method to best achieve the desired outcome. In various embodiments of the present disclosure, the system and method employs both of these methods.

In some examples, the systems and methods described herein may generate operative plans, such as preoperative or intraoperative plans, based on an automated calculation using measurements of distances from anatomical landmarks. For example, the operative plan may include positioning a femoral prosthetic component with respect to a distance from the medial or lateral condyle, and a tibial prosthetic component may be positioned based upon a distance from the tibial tuberosity. In some examples, the preoperative plan may include specific dimensions of anatomical structures of a patient, and/or ranges of measurements, such as anatomical measurements, may be incorporated into an operative plan or provided as a reference for a surgeon. Anatomical distances may be measured by a surgical robot, a health care provider, electronic access device, imaging system, or any other means before or during the surgical procedure, and the system or method may generate suggested prosthetic positioning data and/or an operative plan based on the anatomical distances measured. In some examples, the system or method may generate suggested prosthetic positioning data, bone preparation data such as positioned where the surgeon should cut the bone, and/or an operative plan based (1) age, (2) sex, (3) nationality (to take into account the known distinctly different patterns of anatomy in different ethnic groups), (4) bone density, (5) height, (6) weight, (7) BMI, (8) lower extremity mechanical alignment, (9) lower extremity anatomical alignment, (10) femoral articular surface angle, (11) tibial articular surface angle, (12) mechanical axis alignment strategy, (13) anatomical alignment strategy, (14) natural knee alignment strategy, (15) femoral bowing, (16) tibial bowing, (17) patello-femoral alignment, (18) coronal plane deformity, (19) coronal plane deformity that can be passively correctable, (20) sagittal plane deformity, (21) extension motion, (22) flexion motion, (23) ACL ligament intact, (24) PCL ligament intact, (25) knee motion in all three planes during active and passive range of motion in the joint; (26) three dimensional size, proportions and relationships of joint anatomy in both static and motion, (27) height of the joint line, (28) lateral epicondyle, (29) medial epicondyle, (30) lateral femoral metaphyseal flare, (31) medial femoral metaphyseal flare, (32) proximal tibio-fibular joint, (33) tibial tubercle, (34) coronal tibial diameter, (35) femoral interepicondylar diameter, (36) femoral intermetaphyseal diameter, (37) sagittal tibial diameter, (38) posterior femoral condylar offset-medial and lateral, (39) lateral epicondyle to joint line distance, and/or (40) tibial tubercle to joint line distance.

The system and method of various embodiments of the present disclosure enables or facilitates creating or designing preoperative plans using one or more specific feedback loops not previously used. In one such embodiment, the method generally includes: (a) selecting a plurality of preoperative plans for creating or designing a future preoperative plan; (b) aggregating the results of or feedback based on each actual use of each of the selected preoperative plans; (c) analyzing each preoperative plan compared to the aggregate result to obtain reliable or comparative information; and (d) providing the resulting information back for use in modifying each of the plurality of preoperative plans to automatically and/or manually create or design more accurate initial preoperative plans through this feedback loop.

The system and method of various embodiments of the present disclosure includes selecting an optimal electronic or digital initial preoperative plan (which can be locally based or stored, server based or stored, cloud based or stored, or otherwise electronically or digitally based or stored) for a specific surgical procedure and creating a physical or virtual model that represents the application of the initial preoperative plan on an individual patient's anatomy. The system and method then electronically provides or releases this selected initial preoperative plan to the surgeon. After this initial preoperative plan has been provided or released to the surgeon for review and to make any changes, and before the actual surgical procedure for the individual patient, the system and method receives any changes to the initial preoperative plan from the surgeon, and incorporates these changes to automatically and/or manually create a secondary preoperative plan and a secondary physical or virtual model. In some examples, changes to the preoperative plan may be completed after initiating the surgical procedure. For example, a surgeon may have completed a cut into the patient's tibia, and as a result of the surgeon's or a surgical robot's evaluation of the patient's cartilage the preoperative plan is changed to account for the evaluation of the patient's cartilage. In some examples, the type of surgery may be changed in the operative plan based on data acquired during the surgical operation, such as a partial knee replacement plan may be updated to a total knee replacement plan based on data acquired during the surgical operation.

In some examples, changes to the operative plan may occur after an initial or secondary preoperative plan has been provided or released to the surgeon for use in a surgical procedure for the individual patient. For example, a surgeon, a robotic system or a surgical robot working independently or together may collect new data, such as soft tissue tension, ligament integrity, range of motion of the joint or quality of the articular cartilage prior to completing the surgical procedure, and incorporate this new data into the operative plan, such as by automatically creating a new tertiary preoperative plan and/or a tertiary physical or virtual model to be used on this individual patient during this same operation.

The system and method of various embodiments of the present disclosure includes providing this received information on changes to the initial preoperative plan and physical or virtual model in a first automated electronically transmitted feedback loop (that may employ the use of any type of conventional server, physical flash drives, Internet wired or wireless data transfer, data transfer through physical server, data transfer through cloud-based servers, and/or otherwise electronically or digitally based systems) to enable the system and method to automatically and/or manually create or design more accurate or enhanced future initial preoperative plans and enhanced physical or virtual models for subsequent patients who share specific common features tracked by the system and method. This is the first type of automated feedback loop that the system and method of the present disclosure provides to improve surgical procedure preoperative plans that are subsequently used as part of preoperative plan sets to create aggregated preoperative plans.

After the actual surgical procedure for the individual patient takes place, the system and method of various embodiments of the present disclosure also receives any further changes to the secondary preoperative plan and model that are actually implemented in the operating room. The system and method includes providing this further received information on changes to the secondary preoperative plan and physical or virtual model in a second automated electronic feedback loop (that may employ any type of conventional server, the use of physical flash drives, Internet wired or wireless data transfer, data transfer through physical server, data transfer through cloud-based servers, and/or otherwise electronically or digitally based systems) to enable the system and method to automatically and/or manually create or design more accurate or enhanced future initial preoperative plans and enhanced physical or virtual models for subsequent patients who share specific common features tracked by the system and method. This is the second type of automated feedback loop that the system and method of the present disclosure provides to improve surgical procedure preoperative plans that are subsequently used as part of preoperative plan sets to create aggregated preoperative plans.

After the actual surgical procedure for the individual patient is completed and after the surgeon obtains actual feedback from the patient regarding the actual results of the surgery and the patient's recovery, the system and method of various embodiments of the present disclosure, also receives such information. This information includes a wide range of different information such as patient clinical outcome information on the results of the operation, including imaging techniques, personal health trackers, wearable sensors, biometric sensors, patient reported outcomes and outcome measurement tools.

The system and method of various embodiments of the present disclosure includes providing this further received patient result information in a third automated electronic feedback loop (that may employ the use of any type of conventional server, physical flash drives, Internet wired or wireless data transfer, data transfer through physical server, data transfer through cloud-based servers, and/or otherwise electronically or digitally based systems) to enable the system and method to automatically and/or manually create or design more accurate or enhanced future initial preoperative plans and enhanced physical or virtual models for subsequent patients who share specific common features tracked by the system and method. This is the third type of automated feedback loop that the system and method of the present disclosure provides to improve surgical procedure preoperative plans that are subsequently used as part of preoperative plan sets to create aggregated preoperative plans.

According to one aspect of the present disclosure, a computer-implemented method for optimizing a future surgical preoperative plan is disclosed. The computer-implemented method may include providing, via a server, a selection of an optimal electronic initial preoperative plan for a robotic surgical procedure. The surgical procedure may include implanting an implant and/or prosthesis into a patient with the assistance of a robot. The method may also include electronically, via a server and an electronic access device, providing an electronic initial preoperative plan to a surgical robot. The method may also include receiving, prior to the surgical procedure and via an electronic access device, information regarding the initial preoperative plan from a surgeon or a surgical robot. In addition, the method may include executing an algorithm, via a server, to create a secondary preoperative plan incorporating information from the surgeon or surgical robot, and providing, via a server and an electronic access device, a secondary preoperative plan to a surgical robot. The method may further include storing in a server and/or an electronic access device information from the surgical robot and/or the surgeon for use in creating a preoperative plan for a subsequent patient who shares at least one common feature with the individual patient, and receiving, during the surgical procedure for the individual patient and via the electronic access device and/or the surgical robot, patient surgical information. In addition, the method may include storing in a server and/or an electronic access device patient surgical information for use in creating a preoperative plan for a subsequent patient who shares at least one common feature with the individual patient. Patient surgical information may include preoperative, intraoperative, and/or postoperative data.

In other aspects of the present disclosure, the computer-implemented method may include one or more of the features below. The method may include executing an algorithm using the patient surgical information, via a server and during a surgical procedure for the individual patient, to create a tertiary preoperative plan, and may further include providing, via a server and an electronic access device, the tertiary preoperative plan to the surgical robot. The method may include displaying, via an electronic access device or the surgical robot, the tertiary preoperative plan to the surgeon during the surgical procedure. The method may also include storing in the server and/or the electronic access device the tertiary preoperative plan for use in creating a preoperative plan for a subsequent patient who shares at least one common feature with the individual patient. The surgical procedure may be an osteotomy procedure. The surgical robot may include a robotic assisted device, a computer assisted device, an autonomous robotic device, or a digital surgery platform. The method may further include receiving, after the surgical procedure and via the server, the surgical robot, or the electronic access device, information regarding the results of the surgical procedure from the patient; executing an algorithm, via the server, surgical robot, or electronic access device, to create an updated preoperative plan incorporating the information regarding the results of the surgical procedure from the patient; and storing in the server and/or the electronic access device the updated preoperative plan for use in creating a preoperative plan for a subsequent patient who shares at least one common feature with the individual patient. The method may also include executing an algorithm, via the server, to create a virtual model of the patient's anatomy incorporating the information from the surgeon or surgical robot and representing an application of the secondary preoperative plan; providing, via the server and the electronic access device, the virtual model to the surgical robot or the electronic access device; displaying, via the electronic access device or the surgical robot, the virtual model to the surgeon during the surgical procedure; and storing in the server and/or the electronic access device the virtual model for use in creating a virtual model for a subsequent patient who shares at least one common feature with the individual patient.

The method may also include displaying a virtual model to a surgeon including displaying an augmented reality of the surgical procedure. The algorithm may include the aggregation of preoperative plans, surgical measurements, and patient outcomes stored on the server from prior surgical procedures involving patients who share at least one common feature with the individual patient. The algorithm may include analysis of preoperative plans, surgical measurements, and patient outcomes stored on the server from prior surgical procedures involving patients who shares at least one common feature with the individual patient, wherein the analysis includes using Statistical Natural Language Processing (SNLP), Bayesian aggregation, Machine learning, artificial intelligence, self-learning, Neural Networks, Deep recurrent neural networks, basic reinforcement learning, and deep reinforcement learning. The patient surgical information may include the patient's range of motion; intraoperative data on the patient's soft tissue conditions, angular deformities, flexion contracture, recurvatum, limited flexion, varus, valgus, joint flexibility, laxity, or ability to passively correct a deformity. The information regarding the results of a surgical procedure from a patient may include electronic medical records (EMR) data, data related to the knee society clinical rating system (KSS), data related to the Western Ontario and McMaster Universities osteoarthritis index (WOMAC), HOOS scores, KOOS scores, Harris Hip Scores, SF-12 scores, Sf-36 scores, wearable sensor data, patient self reported data, or imaging data from medical images of the patient. The method may further include providing, via the server and the electronic access device, suggestions to modify a secondary preoperative plan to a surgical robot during a surgical procedure based on patient surgical information. The patient surgical information may include data relating to the patient's soft tissue, range of motion, deformity, measured resection, mechanical axis, natural knee alignment, or gap balancing. The method may also include selecting an optimal electronic initial preoperative plan for a robotic surgical procedure includes receiving and analyzing, via the server, genomic data of the patient or surface mapping data from images of the patient's anatomy. The method may also include displaying, via an electronic access device or a surgical robot, a real-time image of the patient's anatomy to the surgeon during the surgical procedure.

The patient surgical information may include medical imaging data of the patient. In some examples, the patient information regarding the initial preoperative plan from the surgeon or surgical robot may include at least one of the patient's femoral articular surface angle, tibial articular surface angle, femoral bowing, tibial bowing, patella-femoral alignment, coronal plane deformity, sagittal plane deformity, extension motion, flexion motion, ACL ligament, PCL ligament, knee motion in all three planes during active and passive range of motion in the joint, height of the joint line, lateral epicondyle, medial epicondyle, lateral femoral metaphyseal flare, medial femoral metaphyseal flare, proximal tibio-fibular joint, tibial tubercle, coronal tibial diameter, femoral interepicondylar diameter, femoral intermetaphyseal diameter, sagittal tibial diameter, posterior femoral condylar offset-medial and lateral, lateral epicondyle to joint line distance, and tibial tubercle to joint line distance. In some examples, the surgical procedure may include the placement of an implant of autologous tissue, allograft tissue, or synthetic materials; a cardiac, orthopedic, neurologic, urologic, ophthalmologic, obstetric and gynecologic, otolaryngology, plastic, or general surgical procedure; and/or a valve replacement or a transcatheter aortic valve replacement (TAVR) procedure.

In other aspects, a computer-implemented method for optimizing a future surgical preoperative plan may include providing, via a server, a selection of an optimal electronic initial preoperative plan for a surgical procedure. The surgical procedure may include implanting an implant and/or prosthesis into a patient with the assistance of a robot. The method may also include creating, via a server, a patient specific implant design and/or prosthesis design; electronically, via the server and an electronic access device, providing the electronic initial preoperative plan and the implant design and/or prosthesis design to a surgical robot; receiving, prior to the surgical procedure and via the electronic access device or surgical robot, information regarding the initial preoperative plan and/or the implant design and/or prosthesis design from the surgical robot; executing an algorithm, via the server, to create a secondary preoperative plan and a secondary implant design and/or prosthesis design incorporating the information from the surgical robot; providing, via the server and the electronic access device, the secondary preoperative plan and the secondary implant design and/or prosthesis design to the surgeon or surgical robot; storing in the server and/or the electronic access device the information from the surgical robot for use in creating a preoperative plan and/or implant design and/or prosthesis design for a subsequent patient who shares at least one common feature with the individual patient; identifying an implant and/or prosthesis for use in the surgical procedure based on the secondary implant design and/or the secondary prosthesis design; and storing in the server and/or the electronic access device the built or selected implant and/or prosthesis design for use in creating a preoperative plan and/or implant and/or prosthesis design for a subsequent patient who shares at least one common feature with the individual patient.

In other aspects, the method for optimizing a future surgical preoperative plan may include creating a patient specific implant design and/or prosthesis design including matching the patient's arc of curvature of the native femoral condyle with an arc of curvature of the implant and/or prosthesis. The method may also include creating an implant design and/or prosthesis design using medical images of the patient and an algorithm that includes the aggregation of preoperative plans, surgical measurements, medical images, and patient outcomes stored on the server from prior surgical procedures involving patients who shares at least one common feature with the individual patient.

In other aspects of the present disclosure, a computer-implemented method for optimizing a future surgical preoperative plan is disclosed. In some examples, the method may include providing, via a server, a selection of an optimal electronic initial preoperative plan for a surgical procedure. The surgical procedure may include implanting an implant and/or prosthesis into a patient with the assistance of a robot. The method may also include creating, via the server, a patient specific surgical instrument design; electronically, via the server and an electronic access device, providing the electronic initial preoperative plan and the surgical instrument design to a surgical robot; receiving, prior to the surgical procedure and via an electronic access device or surgical robot, information regarding the initial preoperative plan and/or the surgical instrument design; executing an algorithm, via the server, to create a secondary preoperative plan and a secondary surgical instrument design incorporating the information; providing, via the server and the electronic access device, the secondary preoperative plan and the secondary surgical instrument design to the surgeon or surgical robot; storing in the server and/or the electronic access device the information for use in creating a preoperative plan and/or surgical instrument design for a subsequent patient who shares at least one common feature with the individual patient; identifying a surgical instrument for use in the surgical procedure based on the secondary surgical instrument design; and storing in the server and/or the electronic access device the built or selected surgical instrument design for use in creating a preoperative plan and/or surgical instrument design for a subsequent patient who shares at least one common feature with the individual patient.

Other objects, features and advantages of the present invention will be apparent from the following detailed disclosure, taken in conjunction with the accompanying sheets of drawings, wherein like reference numerals refer to like parts.

The foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

DETAILED DESCRIPTION

One example embodiment of the present disclosure provides a robotically assisted surgical procedure planning system and method with multiple feedback loops for automatically optimizing future robotically assisted surgical preoperative plans. This example system and method includes: (a) determining or selecting an optimal electronic initial preoperative plan for a specific robotically assisted surgical procedure and creating a virtual model that represents the application of that initial preoperative plan on an individual patient; (b) electronically providing this selected initial preoperative plan to the surgeon; (c) before the actual surgical procedure for the individual patient takes place, the surgeon reviews the initial preoperative plan and can choose to make changes to that preoperative plan, receiving any changes to the initial preoperative plan from the surgeon; (d) using these received changes to automatically create a secondary preoperative plan and a secondary virtual model (as part of this first automated feedback loop); and (e) electronically providing this secondary preoperative plan and model to the surgeon for use during the robotically assisted surgical procedure. This secondary plan is automatically sent via an electronic feedback loop back for storage in the system to be used as part of a preoperative plan set to create an aggregated preoperative plan for a subsequent patient who shares one or more specific common features with the individual patient. During the period when the actual surgical procedure for the individual patient takes place, the system electronically registers or stores certain individual patient related data found or realized during the initial parts of the surgical procedure or operation, such as range of motion, ligament laxity and deformity. This additional data may cause one or more further changes to the secondary preoperative plan and model in real time that are performed either by the system automatically or by the surgeon, creating a tertiary plan. This tertiary plan is then subsequently implemented during the rest of the actual surgical procedure on the individual patient in the operating room. The tertiary preoperative plan is also automatically sent via an electronic feedback loop back for storage in the system to be used as part of a preoperative plan set to create an aggregated preoperative plan for a subsequent patient who shares one or more specific common features with the individual patient. In various embodiments, this example system and method further includes: (i) after the surgeon obtains actual feedback from the patient regarding the actual results of the surgery and the individual's patients recovery, receiving individual patient clinical outcome information on the results of the surgical procedure; and (ii) automatically using this further received patient clinical outcome information in a further automated feedback loop to automatically create an enhanced future initial preoperative plan and an enhanced virtual model for a subsequent patient who shares one or more specific common features with the individual patient. In certain such embodiments, the system and method can use this further received patient clinical outcome information with integrated connections to surgical outcome registries, patient universal health records, or data from physician or hospital electronic medical record systems to enhance the future individual preoperative plans.

Another example embodiment of the present disclosure provides a patient specific instrumentation system surgical procedure planning system and method with multiple feedback loops for automatically optimizing future patient specific instrumentation system surgical preoperative plans. This example system and method includes: (a) determining or selecting an optimal electronic initial preoperative plan for a specific patient specific instrumentation system surgical procedure and creating a virtual model that represents the application of that initial preoperative plan on an individual patient; (b) electronically providing this selected initial preoperative plan to the surgeon; (c) before the actual surgical procedure for the individual patient takes place, receiving any changes to the initial preoperative plan from the surgeon; (d) using these received changes to automatically create a secondary preoperative plan and a secondary virtual model (as part of this first automated feedback loop); (e) electronically providing this secondary preoperative plan and model for fabrication of a patient specific instrumentation system cutting block instrument; and (f) during the actual surgical procedure for the individual patient takes place, the system and method registering certain data found during the initial parts of the operation, such as range of motion, ligament laxity and deformity. This additional data may cause further changes to the secondary plan and model, performed either by the system automatically or by the surgeon, creating a tertiary plan. This tertiary plan is then implemented during the rest of the actual surgical procedure on the individual patient in the operating room; and (g) the tertiary plan is automatically sent via a feedback loop to the system to be stored and used as part of a preoperative plan set to create an aggregated preoperative plan for a subsequent patient who shares one or more specific common features with the individual patient. In various embodiments, this example system and method further includes: (h) after the surgeon obtains actual feedback from the patient regarding the actual results of the surgery and the individual's patients recovery, receiving individual patient clinical outcome information on the results of the surgical procedure; and (i) automatically using this further received patient clinical outcome information in a further automated feedback loop to automatically create an enhanced future initial preoperative plan and an enhanced virtual model for a subsequent patient who shares one or more specific common features with the individual patient.

Another example embodiment of the present disclosure provides a surgical procedure planning system and method with multiple feedback loops for automatically optimizing future surgical preoperative plans which create patient specific (such as custom) implants and prostheses. This example system and method includes: (a) determining or selecting an optimal electronic initial preoperative plan for a specific surgical procedure and creating a virtual model that represents the application of that initial preoperative plan on an individual patient, creating a patient specific (custom) implant/prosthesis design; (b) electronically providing this selected initial preoperative plan to the surgeon; (c) before the actual surgical procedure for the individual patient takes place, receiving any changes to the initial preoperative plan from the surgeon; (d) using these received changes to automatically create a secondary preoperative plan and a secondary virtual model (as part of this first automated feedback loop); (e) electronically providing this secondary preoperative plan, model and patient specific (custom) implant/prosthesis design to the surgeon for use during surgical procedure; (f) during the actual surgical procedure for the individual patient, the system registers certain data found during the initial parts of the operation, such as range of motion, ligament laxity and deformity. This additional data may cause further changes to the secondary plan and model, performed either by the system automatically or by the surgeon, creating a tertiary plan. This tertiary plan is then implemented during the rest of the actual surgical procedure on the individual patient in the operating room; and (g) the tertiary plan is automatically sent via a feedback loop to the system to be used as part of a preoperative plan set to create an aggregated preoperative plan for a subsequent patient who shares one or more specific common features with the individual patient. In various embodiments, this example system and method further includes: (h) after the surgeon obtains actual feedback from the patient regarding the actual results of the surgery and the individual's patients recovery, receiving individual patient clinical outcome information on the results of the surgical procedure; and (i) automatically using this further received patient clinical outcome information in a further automated feedback loop to automatically create an enhanced future initial preoperative plan and an enhanced virtual model for a subsequent patient who shares one or more specific common features with the individual patient.

In one example embodiment, the system and method automatically selects a plurality of different stored preoperative plans from an electronic preoperative plan database for creating or designing an initial preoperative plan for a total knee replacement for an individual patient. The system and method automatically aggregates the results of the plurality of selected preoperative plans into an aggregate to produce an optimal initial preoperative plan for the individual patient's knee requiring surgery given a set a preoperative variables regarding the individual patient. The system and method analyzing each selected preoperative plan compared to the aggregate resulting preoperative plan to obtain comparative information. This comparative information includes one or more comparisons of each preoperative plan to the resulting aggregate preoperative plan. The system and method electronically provides the surgeon this selected initial preoperative plan for the knee surgery. The system and method electronically enables the surgeon to input proposed changes. Those changes to this initial preoperative plan are sent back to the system using a first feedback loop to be included in future aggregation, modeling and optimization for future patient preoperative plans. The surgeon then uses the preoperative plan on their patient and in doing so will record digitally intra-operative information such as: (a) range of motion data; (b) data on angular deformity of the joint; and/or (c) data regarding the ability to passively correct the angular deformity. The system and method uses this intra-operative information to create a tertiary preoperative plan, and this information (both the intra-operative information added and the changes to the preoperative plan that the information produced) are sent back via the feedback loop to be used in future preoperative plans on subsequent patients who share specific common features tracked by the system and where similar intra-operative information is recorded. In this subsequent situation, the system and method uses the aggregation, modeling, and optimization of previous pre-operative plans that had similar intra-operative information recorded to optimize intra-operatively on subsequent patient's preoperative plan and make suggested changes. The system and method electronically provides the surgeon this tertiary preoperative plan for use during the surgical procedure. The system and method uses these further received changes actually implemented during that actual surgical procedure to automatically create a tertiary preoperative plan as part of this second automated feedback loop. The system and method can then use this tertiary preoperative plan as part of a preoperative plan set to create an aggregated preoperative plan for a subsequent patient who shares one or more specific common features with the individual patient. After the actual surgical procedure and after a certain amount of time of patient recovery, the system and method electronically enables the surgeon to input further information regarding the patient's knee and recovery progress in a further feedback loop. This information can for example include: patient outcome measurement tools (such as the Knee Society Score), accessing surgical patient outcome registries, and/or physician or hospital electronic medical records. The system and method uses this further received information to automatically revise or create a fourth preoperative plan as part of this third automated feedback loop. The system and method can then use this fourth preoperative plan as part of a preoperative plan set to create an aggregated preoperative plan for a subsequent patient who shares one or more specific common features with the individual patient.

In various embodiments, the system and method of the present disclosure, after identifying a similar set of aggregated data from those similar preoperative plans, uses its analysis to look at edits and revisions that had to be done to the aggregated preoperative plans and optimizes to create one or more improved preoperative plans for future use. The system and method further enhances this process by analyzing clinical outcome of those aggregated preoperative plans to provide further refinements to the initial preoperative plan being produced for the subsequent patient.

In another example embodiment, a patient has decided to have a total knee replacement performed. The surgeon caring for this patient prefers to use the existing rules for establishing their preoperative plan. As part of the preparation for surgery, the patient has x-rays performed on the limb and a CT Scan. Those electronic imaging studies undergo segmentation to provide identification of boundaries and features as well as identifying specific anatomical features producing an electronic plan. In this example, this can be done by suitable auto-segmentation software or can be performed partially or fully manually. This can be part of the system and method of the present disclosure or done separately from the system or method. This electronic plan is then forwarded to a templating stage, which is done by suitable auto-templating software, but can be done partially or fully manually. The auto-templating software can be continuously or regularly updated from other cases, which have been sent back for their data to be stored in the system. The analysis of the aggregated preoperative plans produces an optimal preoperative plan for this patient's set of data.

The goal of this optimal preoperative plan is to best apply the existing rules for preparing a preoperative plan for this particular patient's anatomy. The preoperative plan is then reviewed by the surgeon. The surgeon may decide no further changes are necessary preoperatively or the surgeon may decide to make any number of changes. Examples of changes made to the initial plan include, changes in the coronal alignment angle of the femoral or tibial components, change in the size of the components, changes in the sagittal alignment angle of the femoral or tibial components, changes in the transverse plane alignment rotational angle of the femoral or tibial components, translating the component anteriorly, posteriorly, proximally or distally, removing more or less bone during the preparation. These changes are recorded and sent back to the system to be stored and used to inform the system for decision making on future cases. This feedback loop improves future cases with similar preoperative data profiles. Next in the operation, prior to making definitive preparations to the bones of the knee, the femur, the tibia, and the patella, the knee is evaluated by assessing its range of motion, if it has a deformity, whether that deformity is passively correctable, completely or partially or none at all. The system then recognizes these inputted changes and makes further changes to the preoperative plan based of these conditions seen in the operating room, while keeping the planning consistent with the existing preoperative planning rules. These changes are recorded and sent back to the system to be stored and used to inform the system for decision making on future cases. This feedback loop improves future cases with similar preoperative data profiles and intra-operative data. The surgeon then begins the preparation of the bones in the knee for implantation of the knee implants or components. The surgeon may need to make further adjustments to the preoperative plan as the surgeon sees the results being produced. If further changes are needed, these changes are recorded and sent back to the system to be stored and used to inform the system for decision making on future cases. This feedback loop improves future cases with similar preoperative data and intra-operative profiles. After the operation has been concluded, there are no further changes to this patient's preoperative plan in this example. However, this patient's clinical outcome and images will be followed at various intervals (e.g., at 6 weeks, 3 months, 1 years and annually throughout the patient's life). These outcomes are recorded and sent back to the system to be stored and used to inform the system for decision making on future cases. This feedback loop improves future cases with similar preoperative data profiles.

In another example embodiment, a patient has decided to have a total knee replacement performed. The surgeon caring for this patient prefers to employ the system and method of the present disclosure to use analysis of one or more previous preoperative plans to produce the best or better patient outcome scores for a current patient. As part of the preparation for surgery, the patient has x-rays performed on the limb and a CT Scan. Those electronic imaging studies undergo segmentation to provide identification of boundaries and features as well as identifying specific anatomical features producing an electronic plan. In this example, this can be done by suitable auto-segmentation software or can be performed partially or fully manually. This can be part of the system and method of the present disclosure or done separately from the system or method. This electronic plan is then forwarded to a templating stage, which is done by suitable auto-templating software but can be done partially or fully manually. The auto-templating software can be continuously or regularly updated by machine learning from other cases which have been sent back for their data to be stored the system. The analysis of the aggregated plans produces an optimal preoperative plan for this current patient's set of data. The goal of this optimal preoperative plan is to produce best patient outcome scores. The preoperative plan is then reviewed by the surgeon. The surgeon may decide no further changes are necessary preoperatively or the surgeon may decide to make any number of changes. These changes are recorded and sent back to the system to be stored and used to inform the system for decision making on future cases. This self-learning based on this feedback loop improves future cases with similar preoperative data profiles. Next in the operation, prior to making definitive preparations to the bones of the knee, the femur, the tibia, and the patella, the knee is evaluated by assessing its range of motion, if it has a deformity, whether that deformity is passively correctable, completely or partially or none at all. The system and method then recognizes these inputted changes and makes further changes to the preoperative plan based of these conditions seen in the operating room. These changes are recorded and sent back to the system to be stored and used to inform the system for decision making on future cases. This self-learning based on these feedback loops improves future cases with similar preoperative data profiles and intra-operative data. The surgeon then begins the preparation of the bones in the knee for implantation of the knee implants. The surgeon may need to make further adjustments to the preoperative plan as the surgeon sees the results being produced. If further changes are needed, these changes are recorded and sent back to the system to be stored and used to inform the system for decision making on future cases. This self-learning based on this feedback loop improves future cases with similar preoperative data and intra-operative profiles. After the operation has been concluded, there are no further changes to this patient's preoperative plan in this example. However, this patient's clinical outcome and images will be followed at various intervals (e.g., at 6 weeks, 3 months, 1 years and annually throughout the patient's life). These outcomes are recorded and sent back to the system to be stored and used to inform the system for decision making on future cases. This self-learning based on this further feedback loop improves future cases with similar preoperative data profiles.

In another example embodiment, a patient is having a total knee replacement. One standard alignment strategy for a total knee that a surgeon typically uses is mechanical axis strategy. However, the system and method recognizes that this particular patient has a profile that includes a markedly valgus femur, a varus tibia with anterior bowing, a very hypotrophic lateral femoral condyle, and an increase in posterior tibial slope. The system and method (based on the feedback loop self learning and in certain embodiments machine learning) uses the aggregated data of previous preoperative plans of similar preoperative data cases, revisions of those similar plans, and the clinical outcome of those similar patients, and produces a preoperative plan that differs from traditional mechanical axis strategy. The system and method recommends following the patient's anatomic alignment for implant placement except internally rotating the femoral component two degrees and decreasing the tibial slope to three degrees. This produces a preoperative plan that the surgeon makes no preoperative changes to. In the operating room, no further changes are necessary, decreasing the operative time. In doing so, this limits the time the patient has to be under anesthesia, this decreases cardiac and pulmonary risk, this shortens the time the wound is open, and decreases the risk of infection. This enables the patient to be more likely to recuperate faster and be more likely to have a good result.

In various embodiments of the present disclosure, the third automated feedback loop is used to automatically create an enhanced future initial preoperative plan and an enhanced virtual model based on aggregated enhanced preoperative plans and models. In various embodiments of the present disclosure, aggregating the results of the enhanced preoperative plans includes automatically aggregating the results of the enhanced preoperative plans using one or more machine learning systems or strategies, or one or more model aggregation systems or strategies (such as but not limited to a Statistical Natural Language Processing (SNLP), and/or Bayesian model aggregation system or strategy).

In various embodiments, the preoperative plans created and enhanced by the system and method of the present disclosure can include, but are not limited to, any of the following procedures: (a) orthopedic procedures; (b) knee replacement procedures; (c) hip replacement procedures; (d) partial knee replacement procedures; (e) partial hip replacement procedures; (f) hip resurfacing procedures; (g) elbow replacement procedures; (h) shoulder replacement procedures; (i) ankle replacement procedures; (i) foot surgery; (j) hand surgery; (k) spine surgery; (l) fracture surgery; (m) reconstructive surgery of joints; (n) cartilage reconstruction procedures; (o) general surgery procedures; (p) cardiovascular procedures; (q) urologic procedures; (r) neurosurgical procedures; (s) abdominal surgery; (t) thoracic surgery; and (u) otolaryngological procedures.

While example embodiments of the present disclosure are discussed herein related to surgical procedures, it should be appreciated that the system and method of the present disclosure can be employed for: (a) non-robotic surgical procedures; (b) robotic assisted surgical procedures; (c) semi-autonomous robotic surgical procedures; and (d) autonomous robotic surgical procedures.

In various embodiments of the present disclosure, the system and method determines an initial preoperative plan for an individual patient by automatically analyzing that individual patient's data and comparing that to aggregated stored patient data to find a best stored preoperative plan and model for that individual patient's preoperative condition. The system and method utilizes the aggregated data to produce an optimized preoperative plan for that set of individual patient conditions. In various embodiments, the system and method uses one or more statistical methods including, but not limited to, analysis of variance to select certain preoperative plans (or features thereof) and models. The system and method of the present disclosure can also use machine learning software or strategies to solve for a designated optimal outcome, such as to provide for the fewest number of subsequent changes to the preoperative plan or best patient reported outcome.

In various embodiments of the present disclosure, the system and method uses or employs electronic measurement data obtained from or based on one or more series of measurements taken from electronic instruments such as, but not limited to electronic sensors, or electronic imaging machines (e.g., x-ray, MRI, etc) that fully or partially automatically measure one or more characteristics of an individual patient feature.

It should be appreciated that in various embodiments, the system and method of the present disclosure determines and revises preoperative plans based on one of the following or a combination of: (a) one or more statistical aggregation methods, (b) predefined preoperative plan set analysis techniques, and/or (c) machine learning and model specification strategies.

In various embodiments, the system and method of the present disclosure takes as inputs a collection of disparate patient information, including but not limited to, a plurality of the following: (1) age, (2) sex, (3) nationality (to take into account the known distinctly different patterns of anatomy in different ethnic groups), (4) bone density, (5) height, (6) weight, (7) BMI, (8) lower extremity mechanical alignment, (9) lower extremity anatomical alignment, (10) femoral articular surface angle, (11) tibial articular surface angle, (12) mechanical axis alignment strategy, (13) anatomical alignment strategy, (14) natural knee alignment strategy, (15) femoral bowing, (16) tibial bowing, (17) patello-femoral alignment, (18) coronal plane deformity, (19) coronal plane deformity that can be passively correctable, (20) sagittal plane deformity, (21) extension motion, (22) flexion motion, (23) ACL ligament intact, (24) PCL ligament intact, (25) knee motion in all three planes during active and passive range of motion in the joint; (26) three dimensional size, proportions and relationships of joint anatomy in both static and motion, (27) height of the joint line, (28) lateral epicondyle, (29) medial epicondyle, (30) lateral femoral metaphyseal flare, (31) medial femoral metaphyseal flare, (32) proximal tibio-fibular joint, (33) tibial tubercle, (34) coronal tibial diameter, (35) femoral interepicondylar diameter, (36) femoral intermetaphyseal diameter, (37) sagittal tibial diameter, (38) posterior femoral condylar offset-medial and lateral, (39) lateral epicondyle to joint line distance, and/or (40) tibial tubercle to joint line distance. The system and method of the present disclosure may use machine vision systems to input or obtain certain of the data for the system to use.

In various embodiments, the system and method of the present disclosure attempts to find a best fit for these preoperative data points in the universe of the previously collected and aggregated stored preoperative plans.

Figure 1:
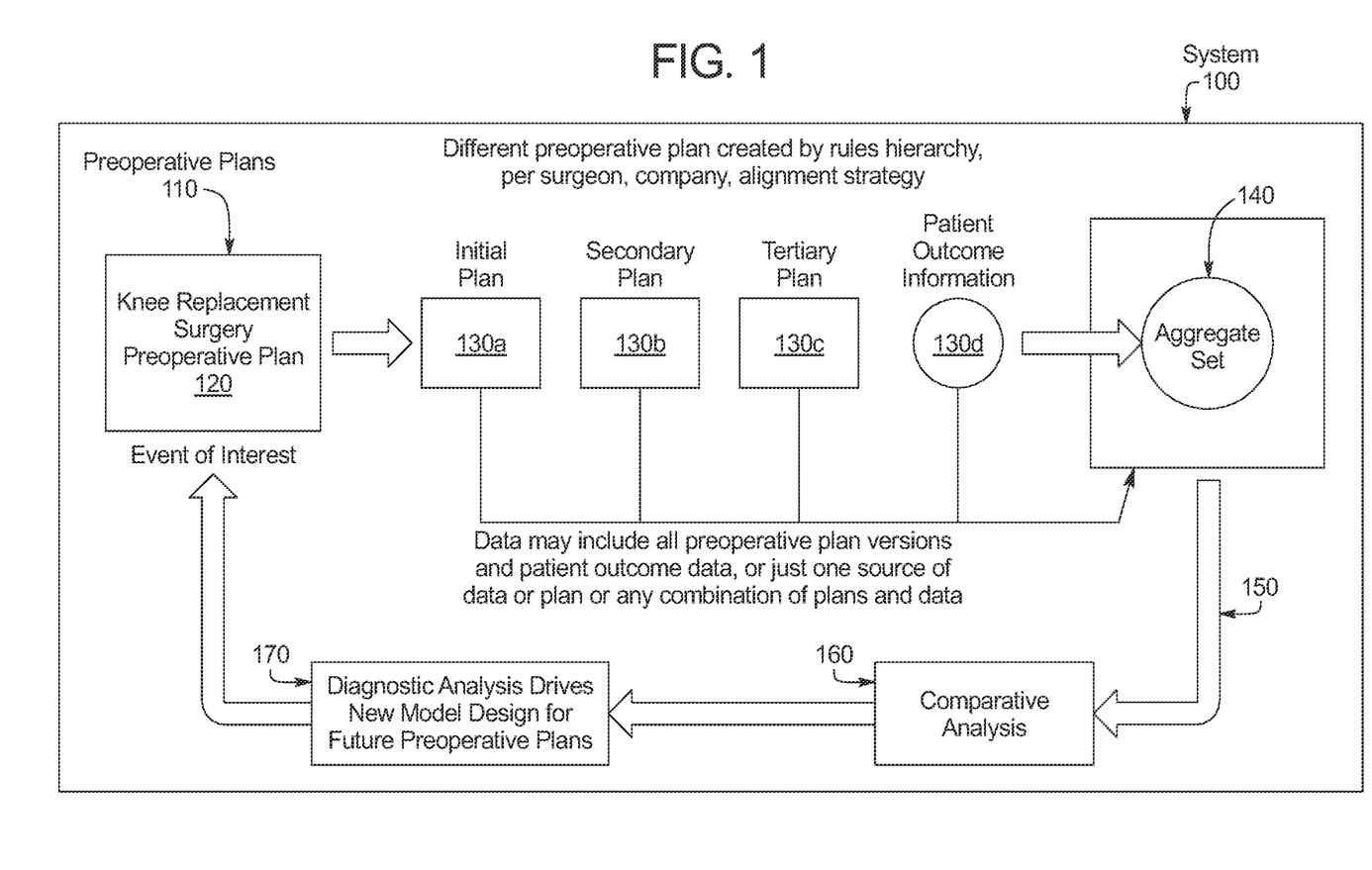
FIG. 1 shows a system work-flow depicting an information feedback loop driving preoperative plan creation or design, in accordance with one example embodiment of the present disclosure.

Referring now to the drawings, FIG. 1 generally shows a system 100 work-flow generally depicting an information feedback loop driving preoperative plan creation or design, in accordance with one example embodiment of the present disclosure. The system 100 includes or stores a set 110 of initial preoperative plans such as knee replacement surgery preoperative plan 120. Electronic sensors and imaging capture data for each of the preoperative plans 110 of the set that are aggregated to create or design a plurality of preoperative plans for initial dissemination. The output or preoperative set 130 (including initial preoperative plan 130a, secondary preoperative plan 130b, and tertiary preoperative plan 130c) of preoperative plans and patient outcome information (130d) provides data for the aggregate set 140. The aggregate set 140 aggregates the results from the further set of preoperative plans 130. In various embodiments, the system and method performs an integrated or comparative analysis 160 that compares the aggregate 140 to each individual model of the plurality of preoperative plans. In various embodiments, the system and method performs a diagnostic analysis 170 to provide evidence to help understand which preoperative plans are optimal for each set of conditions found in preoperative plans. This information is used to refine designs of the future preoperative plans using a feedback loop 150.

Figure 2:
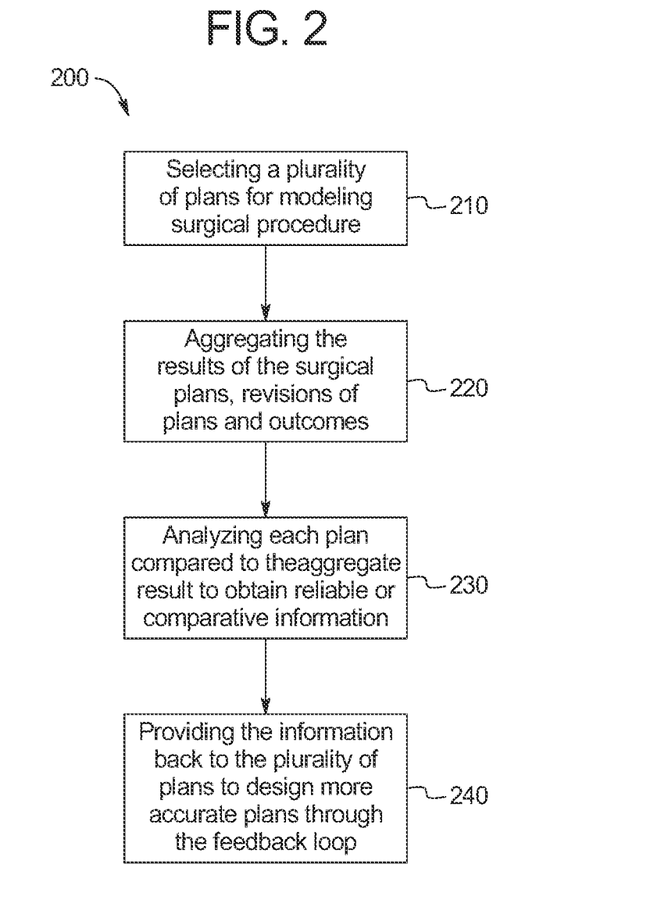
FIG. 2 is a flowchart of a method of creating or designing preoperative plans using a feedback loop, in accordance with one example embodiment of the present disclosure.

FIG. 2 is a flowchart 200 of a method of creating or designing preoperative plans in a feedback loop system in accordance with one embodiment of the present disclosure. As indicated by block 210, several preoperative plans are selected for creating or designing a preoperative plan. As indicated by block 220, the results of the preoperative plans are aggregated. As indicated by block 230, each model analyzed is compared to the aggregate result to obtain reliable or comparative information. As indicated by block 240, the information is provided back to the system for the plurality of preoperative plans through the feedback loop to create or design more accurate future preoperative plans.

Figure 3:
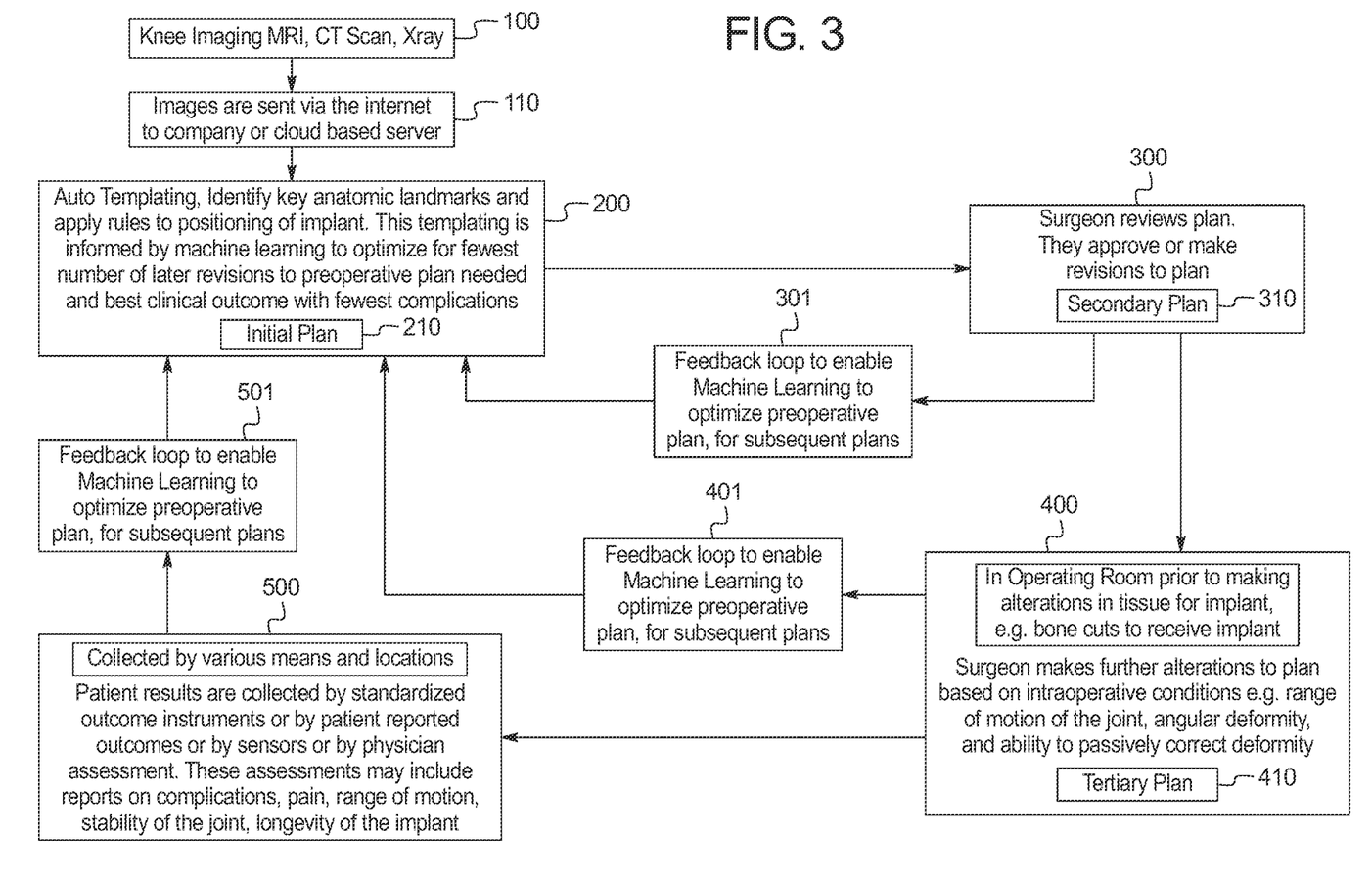
FIG. 3 shows a workflow depicting a feedback loop disclosing the various stages of iteration available to a given preoperative plan and how each iteration can be sent back to the aggregate independently or as part of a complete workflow.

FIG. 3 shows a workflow depicting a feedback loop showing the various stages of iteration available to a given preoperative plan and how each iteration can be sent back to the aggregate independently or as part of a complete workflow. Patient imaging and data 100, is collected and images and/or data are sent via a data network (such as the internet) to the system (which can include a cloud based server) as indicated by block 110. That imaging and/or data is the processed and templating is performed as indicated by block 200. Auto-templating identifies key anatomic landmarks and applies rules to positioning of implant as indicated by block 200. This templating may be informed by machine learning to optimize for fewest number of later revisions to preoperative plan needed and for the best clinical outcome with fewest complications as indicated by block 200. This process produces an initial preoperative plan 210. The system and method forwards this preoperative plan 210 to the surgeon for review as indicated by block 300. The surgeon can approve or modify the initial preoperative plan 210 to create a secondary preoperative plan 310. This secondary preoperative plan 310 is sent back to or maintained by the system via a feedback loop to enable machine learning to optimize future preoperative plans as indicated by block 301. In addition, the secondary plan 310 is forwarded for use in the operating room. In the operating room, the surgeon can make or input further alterations to secondary plan based on intra-operative conditions (e.g., range of motion of the joint, angular deformity, and ability to passively correct deformity) as indicated by block 400 thereby creating a tertiary plan, 410. The tertiary plan 410 is sent back to the system for saving via a feedback loop to enable machine learning to optimize the preoperative plan, for future plans as indicated by block 401. In addition, after a preoperative plan has been executed in the operating room, patient results are collected by standardized outcome instruments, by patient reported outcomes, by sensors or by physician assessment as indicated by block 500. These assessments may include reports on complications, pain, range of motion, stability of the joint, longevity of the implant. This data may be collected by various mechanisms and at multiple locations. This patient outcome information is sent back to the aggregate via another feedback loop to enable machine learning to optimize the preoperative plan for the creation of future preoperative plans as indicated by block 501.

It should be appreciated that various example embodiments of the present disclosure provide a system which generally includes one or more computers (such as one or more servers and one or more memory devices that store one or more databases) configured to communicate with one or more electronic access devices. For purposes of simplicity and brevity, this disclosure primarily describes the system and method of the present disclosure with respect to one surgeon and one patient. However, it should be appreciated that the system and method of the present disclosure is meant to simultaneously work with many surgeons and many patients. The system and method of the present disclosure is expandable to large quantities of surgeons and patients. It should be appreciated that, for implementation with multiple different surgeons and patients, the system and method of the present disclosure will provide suitable secure segregation of patient data for patient privacy and security in accordance with applicable privacy and other legal or regulatory requirements (such as HIPAA compliance).

In various embodiments, the system includes one or more computers such as one or multiple servers configured to communicate through a data network (such as the internet) with a plurality of electronic access devices. In certain embodiments, the system is also configured to communicate with one or more EHR or EMR systems. The computer(s) (such as the server(s)) includes one or more central processing units (not shown) and one or more memory devices (not shown) which store instructions (not shown), and one or more databases (not shown). It should be appreciated that computers or servers employed in the system of the present disclosure may have various configurations and may be cloud based. The present disclosure contemplates that the access devices can include any suitable user computer and/or computerized electronic communication device. Such devices include, but are not limited to: (a) a cellular telephone (such as a smart phone); (b) a tablet-computing device; (c) a laptop computer; and (d) a desktop computer. Users operate these access devices to access or communicate with the system through the data network.

It should be appreciated that in various embodiments, the system operates with the access devices through one or more software programs or applications downloaded to those access devices (i.e., commonly called "apps"). It should be appreciated that in other various embodiments, the system operates with the access devices through one or more software programs or web sites accessible by those access devices. It should be appreciated that in various embodiments, the system operates with the access devices through one or more software programs or applications downloaded to those access devices and through one or more software programs or web sites accessible by those access devices. It should be further appreciated that the system and the user access devices can co-act in other suitable manners in accordance with the present disclosure.

In various embodiments, the system requires each of the users to register with the system. In such embodiments, each user has a user identifier (such as a name or e-mail address) and a password or other identifier to access or use the system.

In various embodiments, the system communicates with the various access devices through one or more suitable wired, partially wired, or wireless data networks. Thus, it should be appreciated that the system of the present disclosure can operate through a suitable central or remote network such as but not limited to one or more local area networks (LANs), one or more wide area networks (WANs), one or more cellular networks, one or more intranets, and/or the internet.

In various embodiments, the system of the present disclosure suitably stores data needed to operate the system in one or more suitable system databases. It should be appreciated that any other suitable database schemes and relationships can be employed in accordance with the present disclosure.

It should be appreciated that the system suitably stores data regarding each of patients in suitable system databases. In various embodiments, all such patient data and communications regarding patient data are encrypted. For example, in certain embodiments, the system encrypts (using 256-bit AES encryption) all patient related data at rest, in transit and in use. It should be appreciated that the system of the present disclosure can encrypt the patient data in other suitable methods.

It should be understood that modifications and variations may be effected without departing from the scope of the novel concepts of the present invention, and it should be understood that this application is to be limited only by the scope of the claims.

In some examples, the aggregation of preoperative plans, measurements, data, secondary preoperative plans, tertiary preoperative plans, final plans and/or outcome measures of surgical procedures creates data which may be analyzed, over a server, on a local electronic access device, electronic surgical device, or surgical robot. In some examples, the disclosed systems and methods may analyze data by methods including but not limited to, Statistical Natural Language Processing, Bayesian aggregation, Machine learning, artificial intelligence, self-learning, Neural Networks, Deep recurrent neural networks, basic reinforcement learning, and/or deep reinforcement learning. In some examples, data, such as preoperative data or intra-operative data, may include data relating to soft tissue, such as range of motion, angular deformities, flexion contracture, recurvatum, limited flexion, varus, valgus, and the ability to passively correct the deformity, joint flexibility and/or laxity. In some examples, pre-operative data may be any information obtained by the surgeon, a surgical robot, the server, the electronic access device or any other means relating to the patient or surgical operation during the performance of the surgery. In some examples, intra-operative data may include information obtained immediately before or immediately after the performance of the surgery, such as data relating to preparation of the patient for surgery or measurements of the patients anatomy made soon after the completion of the surgery. In addition to those discussed above, preoperative data, intra-operative data and/or postoperative data, such as patient data and/or outcome data, may include Electronic Medical Records (EMR) data, data from the Knee Society Clinical Rating System (KSS), data from the Western Ontario and McMaster Universities Osteoarthritis Index (WOMAC), Hoos, Koos, SF-12, SF-36, Harris Hip Score, patient self reported data, biometric data, data from wearable sensors, and/or data from imaging techniques such as Magnetic Resonance Imaging (MRI), radiography, ultrasound, x-ray, thermography, tactile imaging, elastography, nuclear medicine functional imaging, positron emission tomography (PET), single-photon emission computer tomography (SPECT), computed tomography scanning (CT scanning), or other types of medical imaging. In some examples, image data may enable surface mapping of a patient's anatomy, surgical implant, or surgical instrument. Image data may be acquired preoperatively, intra-operatively, or postoperatively. In some examples, the system and/or method may incorporate augmented reality applications such as a virtual model using medical images that utilized real-time surgical data to create an augmented reality using a surgical robot or electronic access device. In other examples, the system and/or method may not include an imaging system.

In some examples, the system or method may include gathering or using patient alignment data such as mechanical axis alignment, anatomic alignment, natural knee alignment, gap balancing, measured resection, and other forms of bodily alignment in preparing preoperative plans, implant designs, medical instrumentation designs, or other recommendations. In some examples, the system or method may include gathering genomic data of the patient or of other patients, such as patients who share at least one common feature with a subject patient. In addition to those noted above, the system or method may be used for osteotomy procedures, computer navigated surgery, neurological surgery, spine surgery, otolaryngology surgery, orthopedic surgery, general surgery, urologic surgery, ophthalmologic surgery, obstetric and gynecologic surgery, plastic surgery, valve replacement surgery, endoscopic surgery, and/or laparoscopic surgery.

In some examples, the system or method may enable optimization of placement of implants of autologous tissue, allograft tissue, and/or synthetic materials. In some examples, the system or method may enable the optimization of implant choice and/or implant placement within the body of a patient. For example, the system or method may select, based on data from previous patients who shares at least one common feature with the subject patient, an implant or implant design to match the anatomy of a patient, such as matching the arc of curvature of the native femoral condyle with the implant arc of curvature. In some examples, the system or method may generate a custom knee implant design, custom hip implant design, custom partial knee or hip implant design, or custom design of any other implant design for any other part of a patient's anatomy.

In some examples, the system or method may be used with a robotic surgical system in robotic assisted surgical procedures; (c) semi-autonomous robotic surgical procedures; (d) autonomous robotic surgical procedures; or (e) manually controlled robotic surgical procedures. For example, the system may include a surgical robot including a robotic arm, which may be operated by a surgeon, semi-autonomously, autonomously, or a combination thereof. In some examples, a surgical robotic system may be used in the systems and methods discussed herein in any of the applications described herein. For example, a surgical robot may display or provide suggestions to a surgeon or other health care provider, via a server, an electronic access device, or the surgical robotic system, regarding changes to the operative plan during the surgical procedure based on intraoperative data collected during the surgical procedure. In some examples, the system or method may be used with a surgical robotic system including a robotic arm configured for partial knee replacement, partial hip replacement, total knee replacement, and/or total hip replacement surgery. A surgical robotic system may include a conventional server, an electronic display, one or more electronic access devices (such as one or more computers), and/or one or more surgical robots.

In some examples, the system and/or method may include the use of a surgical robotic system that includes a haptically controlled robot. In other examples, a surgical robotic system may include one or more haptically controlled features, such as selecting icons on a display or downloading data from a server. For example, the surgical robotic system may include a haptic device such as the Tactile Guidance System™ (TGS™) manufactured by MAKO Surgical Corp., and used to prepare the surface of a patient's bone for insertion of an implant. A haptic device may provide haptic or tactile guidance to guide a surgeon during a surgical procedure. In some examples, a haptic device may be an interactive surgical robotic arm that holds a surgical tool, such as a surgical burr, and is manipulated by the surgeon to perform a procedure on a patient, such as cutting a surface of a bone.

A surgical robotic system, such as any of the computer or robotic systems described herein, may store any changes made to a preoperative plan preoperatively, intraoperatively, or postoperatively. For example, if a surgeon updates a operative plan to account for a particular soft tissue condition of a patient discovered while conducting the surgical procedure, the surgical robotic system will store this update and/or send this update to a server to be stored. In some examples, the surgical robotic system will automatically store any changes made to a preoperative plan, whether the changes are made by a surgeon, by an electronic access device, by a server, by a the surgical robotic system, or any other changes made preoperatively, intraoperatively, or post-operatively.

In some examples, a surgical robotic system may include a robotic arm and an electronic display, and may generate a three-dimensional virtual model of the surgical procedure and display the three-dimensional virtual model on the electronic display. In other examples, the system or method may generate a two-dimensional virtual model or a combination of a two-dimensional and a three-dimensional virtual model of a patient's anatomy. In some examples, intraoperative adjustments to a virtual model may be made by the surgical robotic system, such as by a robotic device, a robotic arm, a electronic user interface, or a server. In some examples, kinematic and soft tissue data may be collected using the surgical robotic system and a virtual model may be updated based on such intra-operative data. In some examples, a robotic surgical system may include a robotic arm that may cut, ablate, bur, or move a patient's anatomy or surgical implant, and may be configured to place an implant within a patient's anatomy. In some examples, the system or method may include generating a preoperative plan for a surgical robot including steps for cutting, ablating, burring, or moving a patient's anatomy with a surgical robot.

In some examples, a robotic surgical system may include generating a virtual model of a patient's anatomy. During a surgical procedure, the disclosed system or method may include a device for measuring positions on a patient's anatomy to modify a virtual model of the patient's anatomy and such a device may be operated by a robotic device or a surgeon.

Any of the systems and methods discussed herein may include a test or evaluation to be completed before the operative plan can be finalized. Such a test or evaluation may be displayed using an electronic access device, a surgical robotic system, a server, or other electronic device and may require the surgeon to complete the test before beginning or continuing a surgical procedure based on an operative plan generated by the system or on data acquired preoperatively or intraoperatively. For example, the system may indicate to the surgeon that one or more anatomical measurements need to be made (such as range of motion, ligament tension, cartilage disease). In such an example, once the surgeon and/or surgical robotic system completes the test, the surgical procedure may continue and the surgeon or surgical robotic system may execute the operative plan. In some examples, the system and/or method may require the surgeon and/or robotic surgical system to complete an assessment of the patient's soft tissue (before, during, or after the surgical procedure), and the system may then confirm or adjust the operative plan based on the results of the soft tissue assessment. In other examples, the system or method may generate a test for the surgeon to complete or prompt the surgeon and/or robotic surgical system to evaluate the patient when a particular threshold patient measurement value is reached, such as prompting or suggesting an intraoperative test for the surgeon to complete when a patient's heart rate exceeds a threshold. In some examples, the system and/or method may automatically create a new preoperative plan and/or new virtual model when a threshold patient measurement value is reached. In this example, the threshold patient measurement value may be any kind of patient measurement described herein and may be measured by a health care provider such as a surgeon, a surgical robotic system, an imaging system, or any other means.

In some examples, the system and/or method may prompt a surgeon, such as through a visual icon or notification displayed using a robotic surgical system, to conduct a test or evaluation of the patient's anatomy. Based on the information from the results of the test or evaluation, the system and/or method may affirm, suggest a change to or automatically update the operative plan.

In some examples, the system and/or method may tie or correlate intraoperative measurements with preoperative measurements. For example, the system and/or method may generate an indication for the surgeon or the robotic system to complete a range of motion test on the patient prior to surgical procedure so that the range of motion test is not required intraoperatively. In some examples, the system may correlate specific measurements of an anatomical structure in the patients body to the planned position of an implant with the same measurement from previous patients who shares at least one common feature with the individual patient to predict potential intraoperative plan adjustments that may be required.

In one example, the system and/or method may be used to generate a preoperative plan for a soft tissue procedure, such as a meniscal repair or removal, tissue tear repairs, oblation, tumor resections, etc. Preoperative data, such as medical imaging data, may indicate that the patient has a soft tissue tear. After the surgical procedure is completed, the system and/or method may record and store in a server, a surgical robot, and/or electronic access device the results of the procedure to correlate the surgical technique with the patient's outcome data. For example, the surgical procedure may include a manually operated robot that records the motions and tills used to complete the surgical procedure, and based on the patient's outcome data, the system may recommend particular motions and tills of the manually operated robot when generating a surgical plan for a similar soft tissue tear procedure. In another example, the system and/or method may generate a preoperative plan for a tumor resection procedure and may require, at any point prior to or during the procedure, a measurement of surrounding tissue to confirm resection boundaries are appropriate.

Embodiments of the subject matter described in this disclosure may be implemented using computer assisted procedures. For example, a computer assisted procedure may include a computer system, surgical robotic system, and a navigation system that the surgeon may use as a tool to complete the surgery. The computer assisted surgery may include an electronic display that may provide visual suggestions to the surgeon preoperatively and/or intraoperatively. For example, a computer assisted surgery may include an imaging system with a display that provides guidance to the surgeon regarding the positioning of the patient, surgical instruments, one or more prosthetics, or a surgical robot. In some examples, an electronic access device and/or a server may be used in a computer assisted procedure. A computer assisted surgery may include a computer program that incorporates systems and/or methods described herein.

In some examples, the system and/or method may generate a virtual boundary and incorporate the virtual boundary into the preoperative plan. A virtual boundary may be generated using a surgical robotic system, a medical imaging system, a server, a electronic access device, and/or by using data from prior patients who shares at least one common feature with the individual patient. A virtual boundary may indicate an area of the patient to be resected, such as an area of soft tissue or bone to be resected, or an area to avoid resecting. In some examples, a virtual boundary may be overlaid on a CT scan dataset (or other non-segmented data) and may be created using data from an implant. A virtual boundary may identify a volume, axis, or plan to resect in order to position an implant.

The systems and methods of the present disclosure may include measurements from implantable sensors that may provide data regarding the patient preoperatively, intraoperatively, or postoperatively. In some examples, an implantable sensor may measure force, torque, displacement, and/or blood flow. In some examples, an implantable sensor may measure prosthetic or implant degradation or structural integrity, position of implant, data relating to the patient's tissue environment, or movement of an implant within the body of the patient. In some examples, implants may be parts of a joint replacement, fracture repair plate, nail, screw fixation, suture, bone graft, ligament graft, or other type of implant.

In some examples, the system and/or method may be used in a ligament transfer procedure. For example, the system and/or method may include using a surgical robotic system to transfer a ligament and the surgical robotic system may record the steps of the procedure. The recorded steps may be compared with patient postoperative data to indicate success or failure of a procedure, and the system and/or method may associate the steps of the ligament transfer procedure with the recorded patient outcome data for use in creating a preoperative plan for a subsequent patient who shares at least one common feature with the individual patient. In some examples, the postoperative data of the patient may include outcome data relating to particular activities of a patient, such a whether the patient is able to walk after a certain amount of time after a total knee replacement.

In some embodiments of the present disclosure, the system and/or method may generate a preoperative plan that includes details regarding the surface preparation of a patient's bone for positioning of an implant. For example, the preoperative plan may include preparation of the patient's bone to create a specific surface texture to facilitate placement of an implant. In some examples, the system and/or method may use data from prior patients who share at least one common feature with the individual patient to generate the individual patient's preoperative plan, such as the surface texture used in a prior patient's procedure and the tendency for an implant to loosen or shift positions within a patient's body after completion of the surgical procedure.

We claim:

1. A computer-implemented method for optimizing a future surgical preoperative plan, said method comprising:
storing an electronic initial preoperative plan for a robotic surgical procedure, wherein the surgical procedure includes cutting tissue for receiving an implant and/or prosthesis with the assistance of a surgical robot;
receiving, prior to the surgical procedure, information regarding the initial preoperative plan from the surgical robot including information related to a prior movement of the surgical robot to assist in cutting tissue and/or preparing a bone for implant and/or prosthesis insertion;
creating a secondary preoperative plan incorporating the information from the surgical robot;
executing the secondary preoperative plan including 1) moving the surgical robot to cut, ablate, bur, or move a patient's anatomy; and/or 2) moving the surgical robot to move the implant or prosthesis; and
storing information from the surgical robot for use in creating a preoperative plan for a subsequent patient who shares at least one common feature with the individual patient.

2. The method of claim 1, wherein the surgical robot is manipulated by a surgeon.

3. The method of claim 1, wherein the surgical robot includes a robotic arm configured to hold a surgical tool.

4. The method of claim 1, wherein the surgical robot includes a surgical burr configured to cut a bone surface.

5. The method of claim 1, wherein the surgical robot is configured to provide haptic or tactile guidance to guide a surgeon during the surgical procedure.

6. The method of claim 1, further comprising:
storing patient surgical information for use in creating the preoperative plan for the subsequent patient, the patient surgical information including preoperative, intraoperative, and/or postoperative data.

7. The method of claim 6, wherein the patient surgical information includes range of motion data, medical imaging data, soft tissue conditions, angular deformities, measured resection, flexion contracture, recurvatum, limited flexion, varus, valgus, joint flexibility, laxity, ability to passively correct a deformity, mechanical axis, natural knee alignment, and/or gap balancing.

8. The method of claim 6, wherein the patient surgical information includes bone density, extremity mechanical alignment, lower extremity anatomical alignment, femoral articular surface angle, tibial articular surface angle, mechanical axis alignment strategy, anatomical alignment strategy, natural knee alignment strategy, femoral bowing, tibial bowing, patello-femoral alignment, coronal plane deformity, coronal plane deformity that can be passively correctable, sagittal plane deformity, extension motion, flexion motion, ACL ligament intact, PCL ligament intact, knee motion in all three planes during active and passive range of motion in the joint, three dimensional size, proportions and relationships of joint anatomy in both static and motion, height of the joint line, lateral epicondyle, medial epicondyle, lateral femoral metaphyseal flare, medial femoral metaphyseal flare, proximal tibio-fibular joint, tibial tubercle, coronal tibial diameter, femoral interepicondylar diameter, femoral intermetaphyseal diameter, sagittal tibial diameter, posterior, femoral condylar offset-medial and lateral, lateral epicondyle to joint line, distance, and/or tibial tubercle to joint line distance.

9. The method of claim 1, further comprising:
identifying anatomic landmarks, wherein moving the surgical robot is based on the identified anatomic landmarks.

10. The method of claim 9, further comprising imaging the patient's anatomy using a medical imaging device, wherein identifying anatomic landmarks is based on the imaging of the patient's anatomy.

11. The method of claim 9, wherein the identified anatomic landmarks include a medial and/or lateral condyle, and moving the surgical robot to move the implant or prosthesis includes moving the surgical robot to position a femoral implant or prosthesis with respect to a distance from the identified medial and/or lateral condyle.

12. The method of claim 9, wherein the identified anatomic landmarks include a tibial tuberosity, and moving the surgical robot to move the implant or prosthesis includes moving the surgical robot to position a tibial implant or prosthesis with respect to a distance from the identified tibial tuberosity.

13. The method of claim 1, wherein the surgical procedure includes a knee replacement surgery, and the implant and/or prosthesis is a tibial implant and/or prosthesis.

14. The method of claim 1, wherein the surgical procedure includes a knee replacement surgery, and the implant and/or prosthesis is a femoral implant and/or prosthesis.

15. The method of claim 1, wherein the surgical procedure includes a hip replacement surgery.

16. The method of claim 1, wherein the surgical procedure includes a spine surgery.

17. A computer-implemented method for optimizing a future surgical preoperative plan, said method comprising:
  creating a preoperative plan based on 1) prior movement of a surgical robot to assist in cutting a patient's anatomy for receiving an implant and/or preparing a bone for the implant and/or prosthesis insertion, and 2) an initial preoperative plan previously stored;
  executing the preoperative plan, wherein executing the preoperative plan includes controlling a surgical robot configured to cut, ablate, bur, or move a patient's anatomy; and
  storing intra-operative information including patient surgical information and information related to the movement or control of the surgical robot, wherein:
    the future surgical preoperative plan is based on the stored intra-operative information,
    the future surgical preoperative plan includes instructions for controlling or moving the surgical robot, and
    at least some of the intraoperative information is received from the surgical robot.

18. The method of claim 17, wherein the surgical robot is manipulated by the surgeon.

19. A computer-implemented method for optimizing a future surgical preoperative plan, said method comprising:
  creating a preoperative plan based on 1) prior movement of a surgical robot to assist in cutting a patient's anatomy for receiving an implant and/or preparing a bone for the implant and/or prosthesis insertion, and 2) a prior preoperative plan;
  executing the preoperative plan, wherein executing the preoperative plan includes controlling the surgical robot to 1) cut, ablate, bur, or move a patient's anatomy; and/or 2) move the implant or prosthesis; and
  storing intra-operative information including patient surgical information and information related to the movement or control of the surgical robot and/or the surgical tool for use in a future preoperative plan, wherein at least some of the intra-operative information is collected by the surgical robot.

20. The method of claim 18, wherein controlling the surgical robot to move the implant or prosthesis includes controlling the surgical robot to move the implant or prosthesis with respect to a distance from an identified bone landmark.

* * * * *